United States Patent [19]

North et al.

[11] Patent Number: 4,963,546
[45] Date of Patent: Oct. 16, 1990

[54] KETONE DERIVATIVES WHICH ARE ANTAGONISTS OF 5-HT AT 5-HT$_3$ RECEPTORS, COMPOSITIONS CONTAINING THEM, AND METHOD OF USE

[75] Inventors: Peter C. North; Alexander W. Oxford, both of Royston; David J. Cavalla, London; David E. Bays, Ware, all of England

[73] Assignee: Glaxo Group Limited, London, England

[21] Appl. No.: 304,269

[22] Filed: Jan. 31, 1989

[30] Foreign Application Priority Data

Feb. 1, 1988 [GB] United Kingdom ............... 8802127

[51] Int. Cl.$^5$ ............... A61K 31/415; C07D 471/06; C07D 487/06; C07D 487/02
[52] U.S. Cl. ............... 514/214; 514/296; 514/411; 540/581; 546/94; 548/428
[58] Field of Search ............... 546/94; 548/428; 540/581; 514/214, 296, 411

[56] References Cited

U.S. PATENT DOCUMENTS

| | | | |
|---|---|---|---|
| 4,695,578 | 9/1987 | Coates et al. | 514/397 |
| 4,725,615 | 2/1988 | Coates et al. | 514/397 |
| 4,749,718 | 6/1988 | Coates et al. | 514/397 |
| 4,808,581 | 2/1989 | Oxford et al. | 514/212 |
| 4,814,344 | 3/1989 | Humber et al. | 514/397 |

FOREIGN PATENT DOCUMENTS

| | | |
|---|---|---|
| 0242973 | 10/1987 | European Pat. Off. . |
| 0297651 | 1/1989 | European Pat. Off. . |
| 0375045 | 6/1990 | European Pat. Off. . |

*Primary Examiner*—Mark L. Berch
*Attorney, Agent, or Firm*—Bacon & Thomas

[57] ABSTRACT

The invention relates to compounds of the general formula (I):

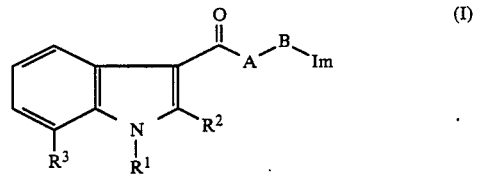

wherein
$R^1$ and $R^2$ together form a $C_{3-5}$alkylene chain and $R^3$ is a hydrogen atom; or
$R^1$ and $R^3$ together form a $C_{2-4}$alkylene chain and $R^2$ is a hydrogen atom;
A-B represents the group $R^4R^5C$—$CH_2$ or $R^4C$=CH;
$R^4$ and $R^5$, which may be the same or different, each represent a hydrogen atom or a $C_{1-6}$alkyl group; and
Im represents an imidazolyl group of formula:

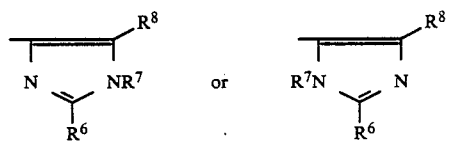

wherein one of the groups represented by $R^6$, $R^7$ and $R^8$ is a hydrogen atom or a $C_{1-6}$alkyl, $C_{3-7}$cycloalkyl, $C_{3-6}$alkenyl, phenyl or phenyl$C_{1-3}$alkyl group and each of the other two groups, which may be the same or different, represents a hydrogen atom or a $C_{1-6}$alkyl group;
and physiologically acceptable salts and solvates thereof.

The compounds are potent and selective antagonists of the effect of 5-HT at 5-HT$_3$ receptors and are useful, for example in the treatment of psychotic disorders, anxiety, and nausea and vomiting.

9 Claims, No Drawings

KETONE DERIVATIVES WHICH ARE ANTAGONISTS OF 5-HT AT 5-HT3 RECEPTORS, COMPOSITIONS CONTAINING THEM, AND METHOD OF USE

This invention relates to ketone derivatives, to processes for their preparation, to pharmaceutical compositions containing them and to their medical use.

In particular the invention relates to ketone derivatives which are potent and selective antagonists of 5-hydroxytryptamine (5-HT) at 5-HT receptors of the type located on terminals of primary afferent nerves. Receptors of this type are now designated as 5-HT$_3$ receptors and are also present in the central nervous system. 5-HT occurs widely in the neuronal pathways in the central nervous system and disturbance of these 5-HT containing pathways is known to alter behavioural syndromes such as mood, psychomotor activity, appetite and memory.

Compounds having antagonist activity at 5-HT$_3$ receptors have been described previously.

Thus for example published European Patent Specification No. 242973 discloses ketone derivatives which may be represented by the general formula:

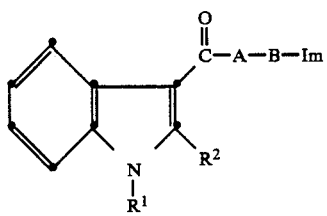

wherein
Im represents an imidazolyl group of formula:

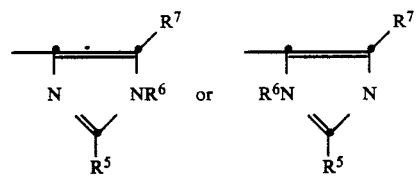

$R^1$ represents a hydrogen atom or a $C_{1-6}$ alkyl, $C_{3-6}$ alkenyl, $C_{3-10}$ alkynyl, $C_{3-7}$ cycloalkyl, $C_{3-7}$cycloalkyl$C_{1-4}$alkyl, phenyl or phenyl$C_{1-3}$alkyl group;
$R_2$ represents a hydrogen atom or a $C_{1-6}$ alkyl, $C_{3-6}$ alkenyl, $C_{3-7}$ cycloalkyl, phenyl or phenyl$C_{1-3}$alkyl group;
A-B represents the group $R^3R^4C-CH_2$ or $R^3C=CH$;
$R^3$ and $R^4$, which may be the same or different, each represents a hydrogen atom or a $C_{1-6}$ alkyl group;
one of the groups represented by $R^5,R^6$ and $R^7$, is a hydrogen atom or a $C_{1-6}$ alkyl, $C_{3-7}$ cycloalkyl, $C_{3-6}$ alkenyl, phenyl or phenyl$C_{1-3}$-alkyl group, and each of the other two groups, which may be the same or different, represents a hydrogen atom or a $C_{1-6}$ alkyl group;
and physiologically acceptable salts and solvates thereof.

We have now found a novel group of compounds which differ in structure from those described previously, and which are potent antagonists of the effect of 5-HT at 5-HT$_3$ receptors.

Thus the present invention provides a ketone derivative of the general formula (I):

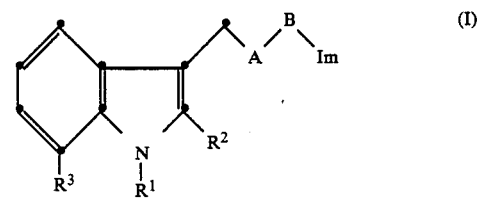

wherein
$R^1$ and $R^2$ together form a $C_{3-5}$ alkylene chain and $R^3$ is a hydrogen atom; or
$R^1$ and $R^3$ together form a $C_{2-4}$ alkylene chain and $R^2$ is a hydrogen atom;
A-B represents the group $R^4R^5C-CH_2$ or $R^4C=CH$;
$R^4$ and $R^5$, which may be the same or different, each represents a hydrogen atom or a $C_{1-6}$ alkyl group;
and Im represents an imidazolyl group of formula:

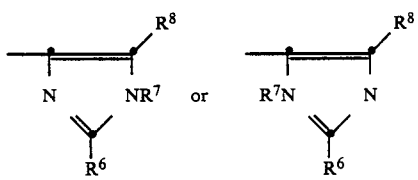

wherein one of the groups represented by $R^6,R^7$ and $R^8$, is a hydrogen atom or a $C_{1-6}$ alkyl, $C_{3-7}$ cycloalkyl, $C_{3-6}$ alkenyl, phenyl or phenyl$C_{1-3}$alkyl group, and each of the other two groups, which may be the same or different, represents a hydrogen atom or a $C_{1-6}$ alkyl group;
and physiologically acceptable salts and solvates thereof.

Suitable physiologically acceptable salts of the compounds of general formula (I) include acid addition salts formed with organic or inorganic acids for example, hydrochlorides, hydrobromides, sulphates, alkyl- or arylsulphonates (e.g. methanesulphonates or p-toluenesulphonates), phosphates, acetates, citrates, succinates, tartrates, fumarates and maleates. The solvates may, for example, be hydrates.

It will be appreciated that, depending on the nature of the substituents $R^4$, $R^5$, $R^6$, $R^7$, $R^8$ and A-B, centres of optical and geometric isomerism may occur in the molecule. All optical isomers of compounds of general formula (I) and their mixtures including the racemic mixtures thereof, and all the geometric isomers of compounds of formula (I), are embraced by the invention.

Referring to the general formula (I), an alkyl group as such or as part of a group may be a straight chain or branched chain alkyl group, for example, methyl, ethyl, propyl, prop-2-yl, butyl, but-2-yl, pentyl, pent-3-yl or hexyl. An alkenyl group may be, for example, a propenyl or butenyl group. It will be appreciated that when $R^7$ represents a $C_{3-6}$ alkenyl group, the double bond may not be adjacent to the nitrogen atom. A phenyl$C_{1-3}$alkyl group may be, for example, a benzyl, phenethyl or 3-phenylpropyl group. A cycloalkyl group may be, for example, a cyclopropyl, cyclobutyl, cyclopentyl, cyclohexyl or cycloheptyl group.

A preferred group of compounds of formula (I) is that in which A-B represents the group $R^4R^5C-CH_2$. A further preferred group of compounds of formula (I)

is that in which $R^4$, and $R^5$ when present, each represent a hydrogen atom.

Another preferred group of compounds of formula (I) is that in which $R^6$, $R^7$ and $R^8$ each independently represent a hydrogen atom or a $C_{1-6}$ alkyl group, more particularly a hydrogen atom or a $C_{1-3}$ alkyl (e.g. methyl) group. A further preferred group of compounds is that wherein $R^6$ and $R^7$ each represent a hydrogen atom and $R^8$ represents a $C_{1-6}$ alkyl (e.g. methyl) group.

Another preferred group of compounds of formula (I) is that in which $R^2$ represents a hydrogen atom, and $R^1$ and $R^3$ together form a $C_{2-4}$ alkylene chain. Within this preferred group of compounds, a particularly preferred group of compounds is that in which $R^1$ and $R^3$ together form the group $-(CH_2)_3-$.

A particularly preferred compound according to the invention is 1-(5,6-dihydro-4H-pyrrolo[3,2,1-ij]quinolin-1-yl)-3-(5-methyl-1H-imidazol-4-yl)-1-propanone.

The potent and selective antagonism of 5-HT at 5-HT$_3$ receptors by compounds of the invention has been demonstrated by their ability to inhibit 3-(5-methyl-1H-imidazol-4-yl)-1-[1-(methyl-t$_3$)-1H-indol-3-yl]-1-propanone binding in rat entorhinal cortex homogenates (following the general procedure described by G. Kilpatrick et al. in Nature, 1987, 330, 746), and/or by their ability to inhibit the 5-HT-induced depolarisation of the rat isolated vagus nerve preparation.

Compounds of formula (I), which antagonise the effect of 5-HT at 5-HT$_3$ receptors, are useful in the treatment of conditions such as psychotic disorders (e.g. schizophrenia and mania); anxiety; and nausea and vomiting, particularly that associated with cancer chemotherapy and radiotherapy. Compounds of formula (I) are also useful in the treatment of gastric stasis; symptoms of gastrointestinal dysfunction such as occur with dyspepsia, peptic ulcer, reflux oesophagitis, flatulence and irritable bowel syndrome; migraine; and pain. Compounds of formula (I) may also be used in the treatment of dependency on drugs and substances of abuse, depression, and dementia and other cognitive disorders.

According to another aspect, the invention provides a method of treatment of a human or animal subject suffering from a psychotic disorder such as schizophrenia or mania; or from anxiety; nausea or vomiting; gastric stasis; symptoms of gastrointestinal dysfunction such as dyspepsia, reflux oesophagitis, peptic ulcer, flatulence and irritable bowel syndrome; migraine; pain; dependency on drugs and substances of abuse; depression; or dementia or another cognitive disorder, which comprises administering an effective amount of a compound of formula (I) or a physiologically acceptable salt or solvate thereof.

Accordingly, the invention also provides a pharmaceutical composition which comprises at least one compound selected from compounds of the general formula (I), and their physiologically acceptable salts and solvates (e.g. hydrates), for use in human or veterinary medicine, and formulated for administration by any convenient route.

Such compositions may be formulated in conventional manner using one or more physiologically acceptable carriers and/or excipients.

Thus the compounds according to the invention may be formulated for oral, buccal, parenteral or rectal administration or in a form suitable for administration by inhalation or insufflation (either through the mouth or nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxylpropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds of the invention may be formulated for parenteral administration by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may also be formulated in rectal compositions such as suppositories or retention enemas, e.g. containing conventional suppository bases such as cocoa butter or other glycerides.

In addition to the formulations described previously, the compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For administration by inhalation the compounds according to the invention are conveniently delivered in the form of an aerosol spray presentation from pressurised packs or a nebuliser, with the use of a suitable propellant, e.g. dichlorodifluoromethane, trichlorofluoromethane, dichlorotetrafluoroethane, carbon dioxide or other suitable gas. In the case of a pressurised aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

For intranasal administration, the compounds according to the invention may be formulated as solutions for administration via a suitable metered or unit dose device or alternatively as a powder mix with a suitable carrier for administration using a suitable delivery device.

The compounds of formula (I) may also be administered in combination with other therapeutic agents. Thus, for example, in the treatment of gastric stasis, symptoms of gastrointestinal dysfunction and nausea and vomiting, the compounds of formula (I) may be administered in combination with antisecretory agents such as histamine $H_2$-receptor antagonists (e.g. ranitidine, sufotidine, 1-methyl-5-[[3-[3-(1-piperidinylmethyl)phenoxy]propyl]amino]-1H-1,2,4-triazole-3-methanol, cimetidine, famotidine, nizatidine or roxatidine) or $H^+K^+$ATPase inhibitors (e.g. omeprazole).

A proposed dose of the compounds of the invention for administration to man (of approximately 70 kg body weight) is 0.001 to 100 mg, preferably 0.01 to 50 mg of the active ingredient per unit dose expressed as the weight of free base, which could be administered, for example, 1 to 4 times per day. It will be appreciated that it may be necessary to make routine variations to the dosage, depending on the age and condition of the patient. The dosage will also depend on the route of administration.

According to another aspect of the invention, compounds of general formula (I), and physiologically acceptable salts or solvates thereof, may be prepared by the general methods outlined hereinafter. In the following description, the groups $R^1$, $R^2$, $R^3$, $R^4$, $R^5$, A, B, and Im are as defined for compounds of general formula (I) unless otherwise stated.

According to a first general process (A), a compound of general formula (I) wherein A-B represents the group $R^4R^5C-CH_2$ and $R^3$ represents a hydrogen atom, may be prepared by reacting a compound of general formula (II):

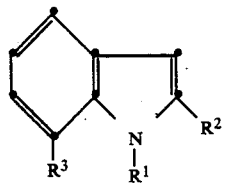

wherein $R^1$ and $R^2$ together form a $C_{3-5}$ alkylene chain and $R^3$ represents a hydrogen atom, or a protected derivative thereof, with an acylating derivative of an acid of general formula (III):

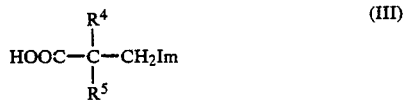

or a salt or protected derivative thereof, followed where necessary by removal of any protecting groups.

Suitable acylating derivatives of the acid (III) include acid halides (e.g. acid chlorides), anhydrides (e.g. symmetrical anhydrides or mixed anhydrides formed for example with pivaloyl chloride), amides, and nitriles.

Thus for example indoles of formula (II) may be acylated according to the Vilsmeier-Haack reaction, using a tertiary amide derivative of an acid of formula (III), such as the corresponding N,N-dimethylpropanamide compound, or a salt thereof, in the presence of a phosphoryl halide such as phosphorus oxychloride. This reaction may be effected in the presence or absence of a solvent. Solvents which may conveniently be employed include halogenated hydrocarbons such as 1,2-dichloroethane. The reaction temperature may be in the range 20° to 100° C.

According to another general process (B), a compound of general formula (I), wherein A-B represents the group $R^4C=CH$, may be prepared by condensing a compound of formula (IV):

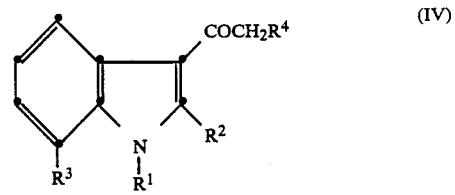

or a protected derivative thereof, with a compound of formula (V):

or a protected derivative thereof, in the presence of a base, followed where necessary by removal of any protecting groups. The reaction may conveniently be effected using an alkali metal hydroxide (e.g. sodium or potassium hydroxide) in an alcohol (e.g. methanol, ethanol or t-butanol) or water, or mixtures thereof, or using an alkali metal alkoxide (e.g. sodium ethoxide or potassium t-butoxide) in the corresponding alcohol (e.g. ethanol or t-butanol) or in an inert solvent such as an ether (e.g. tetrahydrofuran), and at a temperature of 0° to 100° C.

According to another general process (C), a compound of general formula (I) may be converted into another compound of formula (I) using conventional techniques. Such conventional techniques include hydrogenation and alkylation, using protection and deprotection where necessary.

Thus, according to one embodiment of the interconversion process (C), compounds of formula (I) in which A-B represents the group $R^4CH-CH_2$ and $R^6$, $R^7$ and $R^8$ are other than a $C_{3-6}$alkenyl group, may be prepared by hydrogenating the corresponding compounds in which A-B represents the group $R^4CH=CH$. Hydrogenation may also be used to convert an alkenyl substituent into an alkyl substituent. Hydrogenation according to general process (C) may be effected using conventional procedures, for example using hydrogen in the presence of a catalyst, as described in published European Patent Specification No. 242973.

The term 'alkylation' according to general process (C) includes the introduction of groups such as cycloalkyl, alkenyl or phenalkyl groups.

Thus according to another embodiment of the interconversion process (C), a compound of formula (I) in which at least one of $R^4$ and $R^5$ represents a $C_{1-6}$ alkyl group, or a compound in which $R^7$ represents a $C_{1-6}$ alkyl, $C_{3-7}$ cycloalkyl, $C_{3-6}$ alkenyl or phenyl$C_{1-3}$alkyl group may be prepared by alkylating the corresponding compound of formula (I) wherein one or more of R⁴, R⁵ and R⁷ represent a hydrogen atom, using conventional procedures, for example, as described in published European Patent Specification No. 242973. Thus the reactions may be effected using an appropriate alkylating agent of formula $R^9Z$ (wherein $R^9$ is the group to be introduced and Z is a leaving atom or group), preferably in the presence of a base.

It should be appreciated that in the above transformations it may be necessary or desirable to protect any sensitive groups in the molecule of the compound in question to avoid undesirable side reactions. For example, it may be necessary to protect the keto group, for example, as a ketal or a thioketal. It may also be necessary to protect the imidazole nitrogen atom, for example with an arylmethyl (e.g. trityl), alkyl (e.g. t-butyl), alkoxymethyl (e.g. methoxymethyl), acyl (e.g. benzyloxycarbonyl) or a sulphonyl (e.g. N,N-dimethylaminosulphonyl or p-toluenesulphonyl) group.

Thus according to another general process (D), a compound of general formula (I) may be prepared by the removal of any protecting groups from a protected form of a compound of formula (I). Deprotection may be effected using conventional techniques such as those described in 'Protective Groups in Organic Synthesis' by T. W. Greene (John Wiley and Sons, 1981).

For example a ketal such as an alkyleneketal group may be removed by treatment with a mineral acid such as hydrochloric acid. A thioketal group may be cleaved by treatment with a mercuric salt, (e.g. mercuric chloride), in a suitable solvent, such as ethanol. A trityl group may be cleaved by acid hydrolysis (e.g. using dilute hydrochloric or acetic acid). An alkoxyalkyl group may be removed using a Lewis acid such as boron tribromide. An acyl group may be removed by hydrolysis under acidic or basic conditions (e.g. using hydrogen bromide or sodium hydroxide). A sulphonyl group may be removed by alkaline hydrolysis.

Compounds of formula (II) may be prepared, for example, by the methods, or methods analogous to those described by A. B. Smith et al., *Tetrahedron*, 1986, 42, 2957 and P. A. Wender et al., *Tetrahedron*, 1986, 42, 2985.

Compounds of formula (IV) wherein R³ represents a hydrogen atom may be prepared, for example, by treating an indole of formula (II) with an acylating derivative of an acid of formula $R^4CH_2CO_2H$, under conditions analogous to those described in process (A) above.

Compounds of formula (IV) wherein R² represents a hydrogen atom may be prepared, for example, by reaction of a compound of formula (VI):

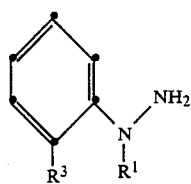

wherein $R^1$ and $R^3$ together form a $C_{2-4}$ alkylene chain, or a salt thereof, with a compound of formula (VII):

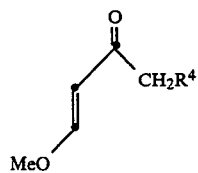

The cyclisation may be carried out in a solvent such as an alcohol (e.g. ethanol) in the presence of an acid catalyst such as an inorganic acid (e.g. concentrated hydrochloric acid) and at a temperature of from 20° to 125° C.

Compounds of formulae (VI) and (VII) are either known, or may be prepared from known compounds by conventional procedures.

Acylating derivatives of the acids of formula (III), as well as the acids (III), and compounds of formula (V) may be prepared, for example, by the methods described in published European Patent Specification No. 242973.

Where it is desired to isolate a compound of the invention as a salt, for example a physiologically acceptable salt, this may be achieved by reacting the compound of formula (I) in the form of the free base with an appropriate acid, preferably with an equivalent amount, in a suitable solvent such as an alcohol (e.g. ethanol or methanol), an aqueous alcohol (e.g. aqueous ethanol), an ester (e.g. ethyl acetate) or an ether (e.g. tetrahydrofuran).

Physiologically acceptable salts may also be prepared from other salts, including other physiologically acceptable salts, of the compound of formula (I) using conventional methods.

Individual enantiomers of the compounds of the invention may be obtained by resolution of a mixture of enantiomers using conventional means, such as an optically active resolving acid; see for example 'Stereochemistry of Carbon Compounds' by E. L. Eliel (McGraw Hill, 1962) and 'Tables of Resolving Agents' by S. H. Wilen.

The methods described above for preparing the compounds of the invention may be used for the introduction of the desired groups at any stage in the stepwise formation of the required compound, and it will be appreciated that these general methods can be combined in different ways in such multi-stage processes. The sequence of the reactions in multi-stage processes should of course be chosen so that the reaction conditions used do not affect groups in the molecule which are desired in the final product.

The invention is further illustrated by the following Examples. All temperatures are in ° C. Thin layer chromatography (t.l.c.) was carried out on silica, and flash column chromatography (FCC) on silica (Merck 9385). Solvent System A as used for chromatography denotes dichloromethane: ethanol: 0.88 ammonia solution. Organic extracts were dried over magnesium sulphate or sodium sulphate.

EXAMPLE 1

1-(2,3-Dihydro-1H-pyrrolo[1,2-a]indol-9-yl)-3-(5-methyl-1H-imidazol-4-yl)-1-propanone maleate A mixture of 2,3-dihydro-1H-pyrrolo[1,2-a]indole (200 mg), N,N-dimethyl-(5-methyl-1H-imidazol-4-yl)propanamide dihydrochloride (323 mg) and phosphorus oxychloride (0.14 ml) was heated at 85° for 1 h. The mixture was allowed to cool and water (40 ml) was added. The solution was washed with dichloromethane (2×40 ml; discarded), basified with 2N sodium carbonate solution and extracted with dichloromethane (3×50 ml). The combined, dried organic extracts were evaporated to give a solid (264 mg) which was purified by FCC eluting with System A to give the free base of the title compound as a solid (180 mg). This was dissolved in hot ethanol (ca. 10 ml) and treated with a solution of maleic acid (73 mg) in ethanol (ca. 2 ml). The solvent was removed in vacuo and the residue was triturated with dry ether (3×20 ml) to give the title compound (245 mg), m.p. 186°–188°.

Water Assay Found 1.152% w/w ≡0.26 mol $H_2O$.
Analysis Found: C,63.8; H,5.7; N,10.0. $C_{18}H_{19}N_3O.C_4H_4O_4.0.26H_2O$ requires C,63.8; H,5.7; N,10.1%.

EXAMPLE 2

3-(5-Methyl-1H-imidazol-4-yl)-1-(7,8,9,10-tetrahydro-6H-azepino[1,2-a]indol-11-yl)propan-1-one maleate A solution of N,N-dimethyl-3-(5-methyl-1H-imidazol-4-yl) propanamide (60 mg) in dichloromethane (0.2 ml) was treated with an excess of ethereal hydrogen chloride. The solvent was removed and the residue was treated with 7,8,9,10-tetrahydro-6H-azepino[1,2-a]indole (60 mg) and phosphorus oxychloride (0.04 ml). The mixture was heated at 85° for 4 h., water (10 ml) was added and the solution was washed with dichloromethane (2×10 ml; discarded). The aqueous layer was basified with 2N sodium carbonate solution and extracted with dichloromethane (3×10 ml). The combined, dried organic extracts were evaporated to give a foam (98 mg) which was purified by FCC eluting with System A (150:10:1) to give a solid (ca. 58 mg). This was dissolved in ethanol (0.5 ml) and treated with a solution of maleic acid (21.5 mg) in ethanol (0.25 ml). The solvent was removed in vacuo and the residue was triturated with dry ether (3×3 ml) to give the title compound (74 mg) m.p. 150°–152°, t.l.c. (System A 150:10:1) Rf 0.35.

EXAMPLE 3

(E)-1-(5,6-Dihydro-4H-pyrrolo[3,2,1-ij]quinolin-1-yl)-3-(5-methyl-1H-imidazol-4-yl)-2-propen-1-one (i) 1-(5,6-Dihydro-4H-pyrolo[3,2,1-ij]quinolin-1-yl)ethanone A mixture of 1-amino-1,2,3,4-tetrahydroquinoline hemisulphate (8.05 g) and 4-methoxy-3-buten-2-one (4.2 ml) in ethanol (50 ml) and conc. hydrochloric acid (9.5 ml) was stirred at 20° for 1 h. The resulting solution was heated under reflux for 4.5 h. The mixture was cooled, concentrated to ca. 10 ml in vacuo and partitioned between ethyl acetate (3×150 ml) and 1M hydrochloric acid (150 ml). The combined organic extracts were evaporated in vacuo to leave an oil (ca. 8 g) which was dissolved in dichloromethane (8 ml) and filtered through a small pad of FCC silica. This silica was then washed with dichloromethane (100 ml). The filtrates were combined and evaporated to leave an oil (ca. 6 g) which was purified by FCC eluting with hexane:ethanol:ammonia (400:100:1) to give an oil (3.5 g). This was crystallised from a mixture of ether:hexane (2:1; 50 ml) to give the title compound (2.2 g), m.p. 108°–110°.

(ii) (E)-1-(5,6-Dihydro-4H-pyrrolo[3,2,1-ij]quinolin-1-yl)-3-(5-methyl-1H-imidazol-4-yl)-2-propen-1-one A solution of potassium hydroxide (0.5 g) in methanol (5 ml) was added to a solution of 1-acetyl-5,6-dihydro-4H-pyrrolo[3,2,1-ij]quinoline (1.1 g) and 5-methyl-1-(triphenylmethyl)-1H-imidazole-4-carboxaldehyde (2.0 g) in methanol (25 ml). The resulting mixture was stirred at 50° for 20 h, heated at reflux for 6 h and then left at 20° for a week. The mixture was diluted with a mixture of acetic acid:water (1:1; 60 ml) and heated on a steam bath for 1 h. The resulting mixture was partitioned between saturated potassium carbonate solution (100 ml) and ethyl acetate (4×100 ml). The combined organic extracts were washed with brine (100 ml), dried and evaporated to leave an oil (3 g) which was purified by FCC eluting with System A (200:8:1 for first 1 l and then 100:8:1) to give the title compound (0.18 g) as a solid, m.p. 90°–100° (decomp.), t.l.c.(ethyl acetate: methanol: triethylamine 80:20:1) Rf 0.32.

EXAMPLE 4

1-(5,6-Dihydro-4H-pyrrolo[3,2,1-ij]quinolin-1-yl)-3-(5-methyl-1H-imidazol-4-yl)-1-propanone maleate A solution of (E)-1-(5,6-dihydro-4H-pyrrolo[3,2,1-ij]quinolin-1-yl)-3-(5-methyl-1H-imidazol-4-yl)-2-propen-1-one (0.18 g) in a mixture of ethanol and methanol (2:1; 20 ml) was hydrogenated over 10% palladium oxide on carbon (5 mg) at room temperature and atmospheric pressure. The catalyst was filtered off and the residue was washed with a further quantity of ethanol (20 ml). The filtrates were combined and evaporated to leave a gum (0.18 g) which was purified by FCC (silica deactivated with triethylamine) eluting with ethyl acetate:methanol (4:1) to give a foam (0.17 g). This was dissolved in ethanol (3 ml) and treated with a solution of maleic acid (0.07 g) in ethanol (1 ml). The resulting solution was diluted with dry ether (4 ml) to precipitate the title compound (0.18 g) as a solid, m.p. 164°–166°.

N.m.r. showed presence of ca. 0.3 mol ethanol.

Analysis Found: C,64.1; H,5.9; N,9.9. $C_{18}H_{19}N_3O.C_4H_4O_4.0.3$ EtOH requires C,64.1; H,5.9; N,9.9%.

The following examples illustrate pharmaceutical formulations according to the invention. The term "active ingredient" is used herein to represent a compound of formula (I).

TABLETS FOR ORAL ADMINISTRATION

Tablets may be prepared by the normal methods such as direct compression or wet granulation.

The tablets may be film coated with suitable film forming materials, such as hydroxypropyl methylcellulose, using standard techniques. Alternatively the tablets may be sugar coated.

Tablets of other strengths may be prepared by altering the ratio of active ingredient to excipients or the compression weight and using punches to suit.

| Direct Compression Tablet | |
|---|---|
| | mg/tablet |
| Active Ingredient | 0.50 |
| Calcium Hydrogen Phosphate BP* | 87.25 |
| Croscarmellose Sodium NF | 1.80 |
| Magnesium Stearate BP | 0.45 |
| Compression weight | 90.00 |

*of a grade suitable for direct compression.

The active ingredient is passed through a 60 mesh sieve, blended with the calcium hydrogen phosphate, croscarmellose sodium and magnesium stearate. The resultant mix is compressed into tablets using a Manesty F3 tablet machine fitted with 5.5 mm, flat bevelled edge punches.

INJECTION FOR INTRAVENOUS ADMINISTRATION

|  | mg/ml | |
|---|---|---|
| Active ingredient | 0.05 | 0.5 |
| Sodium Chloride BP | as required | as required |
| Water for Injection BP to | 1.0 ml | 1.0 ml |

Sodium chloride may be added to adjust the tonicity of the solution and the pH may be adjusted, using acid or alkali, to that of optimum stability and/or facilitate solution of the active ingredient. Alternatively, suitable buffer salts may be used.

The solution is prepared, clarified and filled into appropriate size ampoules sealed by fusion of the glass. The injection is sterilised by heating in an autoclave using one of the acceptable cycles. Alternatively, the solution may be sterilised by filtration and filled into sterile ampoules under aseptic conditions. The solution may be packed under an inert atmosphere of nitrogen or other suitable gas.

We claim:

1. A compound of the formula (I):

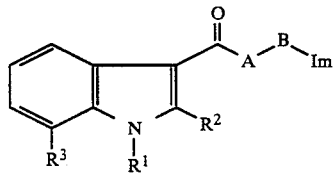

wherein $R^1$ and $R^3$ together form a $C_{2-4}$alkylene chain and $R^2$ is a hydrogen atom;

A-B represents the group $R^4R^5C-CH_2$ or $R^4C=CH$;

$R^4$ and $R^5$, which may be the same or different, each represent a hydrogen atom or a $C_{1-6}$alkyl group; and Im represents an imidazolyl group of formula:

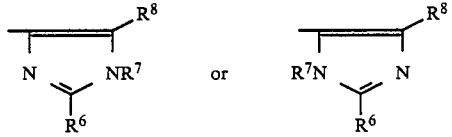

wherein one of the groups represented by $R^6$, $R^7$ and $R^8$ is a hydrogen atom or a $C_{1-6}$alkyl, $C_{3-7}$cycloalkyl, $C_{3-6}$alkenyl, phenyl or phenyl$C_{1-3}$alkyl group and each of the other two groups, which may be the same or different, represents a hydrogen atom or a $C_{1-6}$alkyl group;

or a physiologically acceptable salt or solvate thereof.

2. A compound according to claim 1 in which A-B represents the group $R^4R^5C-CH_2$.

3. A compound according to claim 1 in which $R^4$, and $R^5$ when present, each represent a hydrogen atom.

4. A compound according to claim 1 in which $R^6$, $R^7$ and $R^8$ each independently represent a hydrogen atom or a $C_{1-3}$alkyl group.

5. A compound according to claim 1 in which $R^6$ and $R^7$ each represent a hydrogen atom and $R^8$ represents a $C_{1-6}$alkyl group.

6. A method of treating a condition mediated through 5-HT$_3$ receptors which comprises administering to a patient an effective amount to relieve said condition of a compound of formula (I) as defined in claim 1 or a physiologically acceptable salt or solvate thereof.

7. A compound according to claim 1 in which $R^1$ and $R^3$ together form the group $-(CH_2)_3-$.

8. 1-(5,6-Dihydro-4H-pyrrolo[3,2,1-ij]quinolin-1-yl)-3-(5-methyl-1H-imidazol-4-yl)-1-propanone and physiologically acceptable salts and solvates thereof.

9. A pharmaceutical composition for treating a condition mediated through 5-HT$_3$ receptors which comprises an effective amount to relieve said condition of at least one compound of formula (I) as defined in claim 1 or a physiologically acceptable salt or solvate thereof together with at least one physiologically acceptable carrier or excipient.

* * * * *